United States Patent [19]

Kojima

[11] Patent Number: 5,185,072

[45] Date of Patent: Feb. 9, 1993

[54] ION-SELECTIVE ELECTRODE AND METHOD OF PRODUCING THE SAME

[75] Inventor: Junji Kojima, Kyoto, Japan

[73] Assignee: Horiba, Ltd., Kyoto, Japan

[21] Appl. No.: 725,973

[22] Filed: Jul. 5, 1991

[30] Foreign Application Priority Data

Jul. 7, 1990 [JP] Japan .................... 2-180247

[51] Int. Cl.$^5$ .............................. G01N 27/26
[52] U.S. Cl. ................................ 204/416; 204/420; 204/435
[58] Field of Search ............... 204/416, 418, 420, 433, 204/435

[56] References Cited

U.S. PATENT DOCUMENTS

H745    2/1990  Ishizuka et al. ............... 204/418
4,816,132  3/1989  Kotani et al. ................. 204/420
4,857,166  8/1989  Kotani ......................... 204/435

Primary Examiner—John Niebling
Assistant Examiner—Bruce Bell
Attorney, Agent, or Firm—Price, Gess & Ubell

[57] ABSTRACT

An improved ion-selective electrode assembly and method of preparing the same includes providing a substrate of an insulating material which has a laminated polyethylene terephthalate film layer over an electrically conductive layer. A series of adhering layers is applied over the film layer, with the layer farthest from the substrate being a deoximation silicone room temperature vulcanizing adhesive. Gelatinized internal liquid is positioned in an aperture over the electrically conductive layer, and an ion-responsive glass sheet seals the assembly.

12 Claims, 5 Drawing Sheets

ION-SELECTIVE ELECTRODE AND METHOD OF PRODUCING THE SAME

BACKGROUND OF THE INVENTION

1. Field of the Invention

The present invention relates to an ion-selective electrode that can be incorporated into a monitor for measuring an ion concentration in a sample, such as pH, and a method of producing the same.

2. Description of Related Art

The inventor is aware of various devices for measuring an ion concentration such as pH. Among those devices is an instrument that uses a sheet-type electrode with a flat measuring portion. In the manufacture of this device, the ion-selective electrode is formed with a polyethylene terephthalate (PET) film that is adhered to the glass with one of a family of silicone adhesives. Cross-sections of such structures are disclosed in FIGS. 6(A) and 6(B). As shown in FIG. 6(A), the ion-responsive glass 64 is coated with a layer of a silicone adhesive 63, and then with an overlayer of a primer 62 for adhering the plastic PET film 61.

The embodiment shown in FIG. 6(B) has the PET film 61 covered with a layer of a polyester anchor coating agent 65 and, subsequently, a layer of a polyester family hot melt adhesive 66. This structure is then treated with a silicone family primer 67. Finally, a single liquid dealcoholization-type silicone room temperature vulcanizing adhesive 68 is utilized to adhere the silicone family primer 67 to the ion-responsive glass 64.

Ion-selective electrodes having the above construction frequently have problems in durability. When such electrodes are used in an environment of high temperature and humidity, or in an environment of water of a high temperature, a problem occurs in that the ion-responsive glass 64 is liable to be separated from the PET film 61, and electric installation is frequently deteriorated, reducing the reliability of such an ion-selective electrode.

Thus, there is still a demand for an improvement in providing an ion-selective electrode for measuring instruments.

SUMMARY OF THE INVENTION

The present invention is to provide an improved construction and method of producing an ion-selective electrode having both high reliability and durability.

The improved ion-selective electrode has a substrate of an insulating material supporting a laminated polyethylene terephthalate (PET) film layer with an aperture which has been previously corona treated. An electrically conductive layer or pad is positioned on the substrate and underneath the aperture in the polyethylene terephthalate film layer to provide a terminal for the electrode. A series of adhering layers are progressively applied above the film layer, such as a polyester anchor coating, a polyester hot melt layer, and a silicone primer. A deoximization silicone room temperature vulcanizing adhesive comprises the last layer prior to an ion-responsive glass sheet. A gelatinized internal liquid is positioned within the cavity.

In a method of assembling the ion-selective electrode, the substrate of an insulating material has an electrically conductive layer applied in a defined pattern. The polyethylene terephthalate film is then treated with a corona discharge. This film layer is then laminated onto the substrate with a hole or aperture positioned above an electrically conductive pad. A series of adhering layers is then applied, starting with a polyester anchor coating of approximately 6 to 8 μm thickness, which is then permitted to cure for several minutes. Subsequently, a polyester hot melt layer of approximately 50 μm is applied over the anchor coating layer and again allowed to cure for a few minutes, the curing being at room temperature. A silicone primer is then applied over the hot melt layer and allowed to cure for a few minutes. Finally, a deoximization-type silicone room temperature vulcanizing adhesive is applied and is allowed to cure at room temperature for approximately 48 hours or greater. A gelatinized internal liquid is then inserted into the aperture, and an ion-responsive glass sheet seals the aperture and adheres to the deoximization silicone room temperature vulcanizing adhesive.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an economical and durable ion-selective electrode.

In order to achieve the purposes of the present invention, the present inventor has investigated various combinations of layers of material to form an improved ion-selective electrode. Various combinations of setting-type silicone family adhesives and silicone family primers were tested. The ion-selective electrode of the present invention has a PET film laminated on a PET substrate with an internal electrode formed on a surface thereof. An undercoated treated layer is formed on the surface of the PET film, and an ion-responsive glass is adhered to the surface of the undercoated treated layer by the use of a deoximization-type silicone room temperature vulcanizing adhesive. A cavity in the PET film and surface layers is filled with a gelatinized internal liquid so as to communicate between the ion-responsive glass and the internal electrode. The ion-responsive glass has been appropriately pickled in an acid bath, such as a 5% solution of nitric acid, with ultrasonic flushing for ten minutes and elutes alkaline metals of a reduced quantity.

In production, the PET film is laminated on a PET substrate with an internal electrode formed on a surface thereof. The PET film is subjected to an under-coating treatment of a plurality of layers, and then an ion-responsive glass, which has been appropriately pickled and capable of eluting alkaline metals in a reduced quantity, is adhered to the surface of the undercoating layer by the use of a deoximization-type silicone room temperature vulcanizing adhesive. A gelatinized internal liquid is positioned beneath the ion-responsive glass and above the internal electrode.

As a result of the method of the present invention, an improved ion-selective electrode is provided to provide an adhesion of the ion-responsive glass to the PET film. In the case of an ion-selective electrode for use in the measurement of pH, a quantity of, for example, lithium (Li), which can be eluted from the ion-responsive glass, is reduced so that its durability can be improved.

Figure 1:
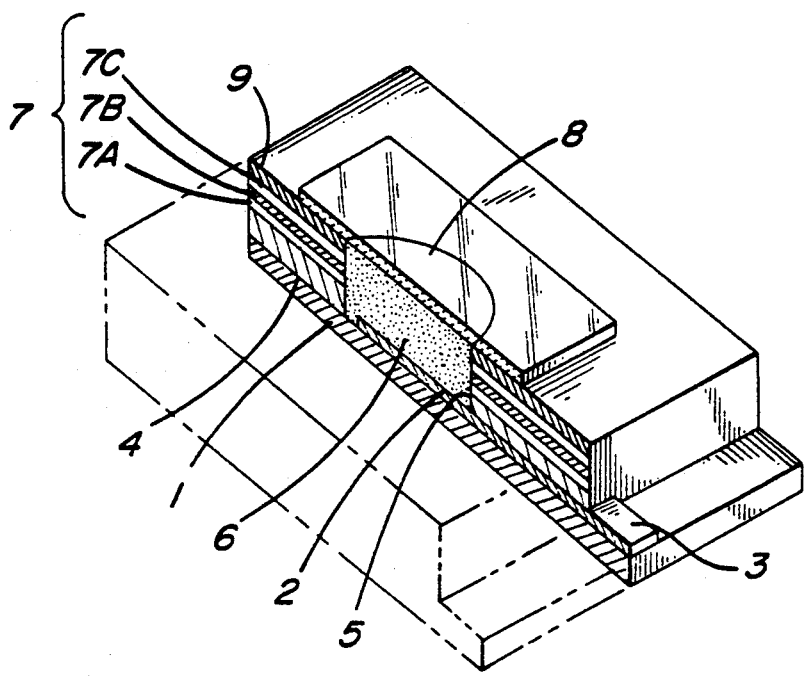
FIG. 1 is a cross-sectional perspective showing a Ph measuring electrode according to the principles of the present invention.

Referring to FIG. 1, a PET printing substrate can be appropriately pretreated and then applied with a silver (Ag) paste by a silk screen printing method to form a plurality of electrically conductive portions (not shown). One of the electrically conductive portions is coated with AgCl to form, for example, a circular pad as an internal electrode. The same silk screen printing procedure can be utilized to extend a portion of the internal electrode 2 as a lead portion 3 on one edge of the printing substrate. A PET film 4, for example, Lumilar, of approximately 188 $\mu$m in thickness, can be subjected to a corona treatment on both sides before application to the substrate 1. Such a material is manufactured and sold commercially by the Toray KK Company of Tokyo, Japan. The PET film 4 is provided with a through hole 5 to define the parameters of the cavity for receiving a gelatinized internal liquid. The PET film 4 is laminated onto the PET printing substrate 1 so that the internal electrode 2 is housed within the hole portion 5.

Figure 2:
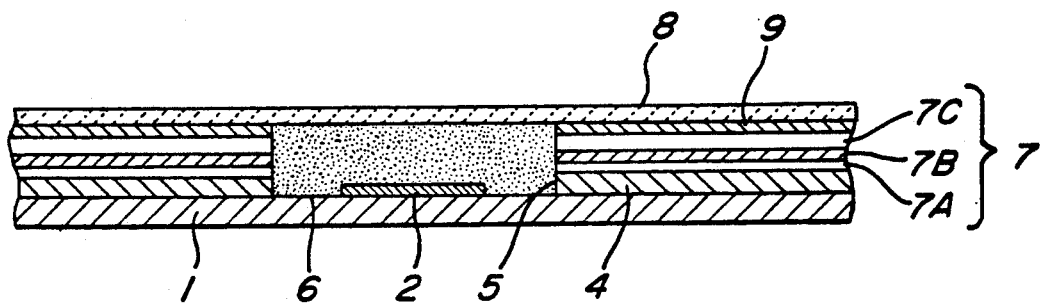
FIG. 2 is a schematic cross-sectional view of a pH measuring electrode disclosed in FIG. 1, taken in a longitudinal direction.

As can be seen in FIG. 2, the gelatinized internal liquid can be charged into the through hole 5 so as to be brought into contact with the internal electrode 2. This gelatinized internal liquid 6 can be composed of a basic internal liquid comprising, for example, AgCl-supersaturated 3.3 N-KCl solution and a phosphate buffer solution with a gelatinizing agent and a gelatinized vaporization preventing agent. Some examples of a gelatinized agent can be agar-agar, gelatin, glue, alginic acid, various kinds of acrylic water-absorptive polymer and the like. Some examples of a gel vaporization-preventing agent can be glycerine, ethylene glycol and the like. This gelatinized internal liquid 6 can be formed into a disk-like shape. In application, the gelatinized internal liquid 6 can be softened into a pasty composition by, for example, a heating step. It can then be charged into the through hole 5, for example, by a screen printing method, so that its upper surface may be projected over an upper surface of the PET film 4.

An undercoated treated layer 7, formed of a series of sublayers, can be formed on the surface of the PET film 4 outside of the internal electrode 2. An example of such an undercoated treated layer can be a polyester family anchoring coating agent 7A applied in a thickness of 6 to 8 $\mu$m. Such a material can be commercially purchased under the trade name Adcoat from Toyo Moton KK of Tokyo, Japan. A polyester family hot melt 7B can then be applied over the coating agent 7A. An example of such a polyester family hot melt is PES 111 EEF, manufactured by Toa Gosei KK of Tokyo, Japan, which is applied in a hot molten configuration to a thickness of 15 $\mu$m. These materials can be respectively cured for a few minutes at room temperature. A primer, such as a plastic silicon family primer, commercially sold as primer C by Toray Dow Corning Silicone KK of Tokyo, Japan, can then be applied as the primer layer 7C, and again cured for a few minutes at room temperature. Next, a deoximization-type silicone RTV adhesive 9 is applied over the primer layer 7C and is cured for 48 hours or more at room temperature. Such a material can be purchased as a silicone adhesive KE-44, manufactured by Shinetsu Kagaku KK of Tokyo, Japan. Finally, a pH-responsive glass such as, for example, pH-responsive glass No. 42, manufactured by Horiba, Ltd. of Kyoto, Japan, can be applied as the surface of the ion electrode. This pH-responsive glass 8 has the characteristic of eluting only a small quantity of alkaline metallic ions, and has been pretreated by a pickling process.

Figure 3:
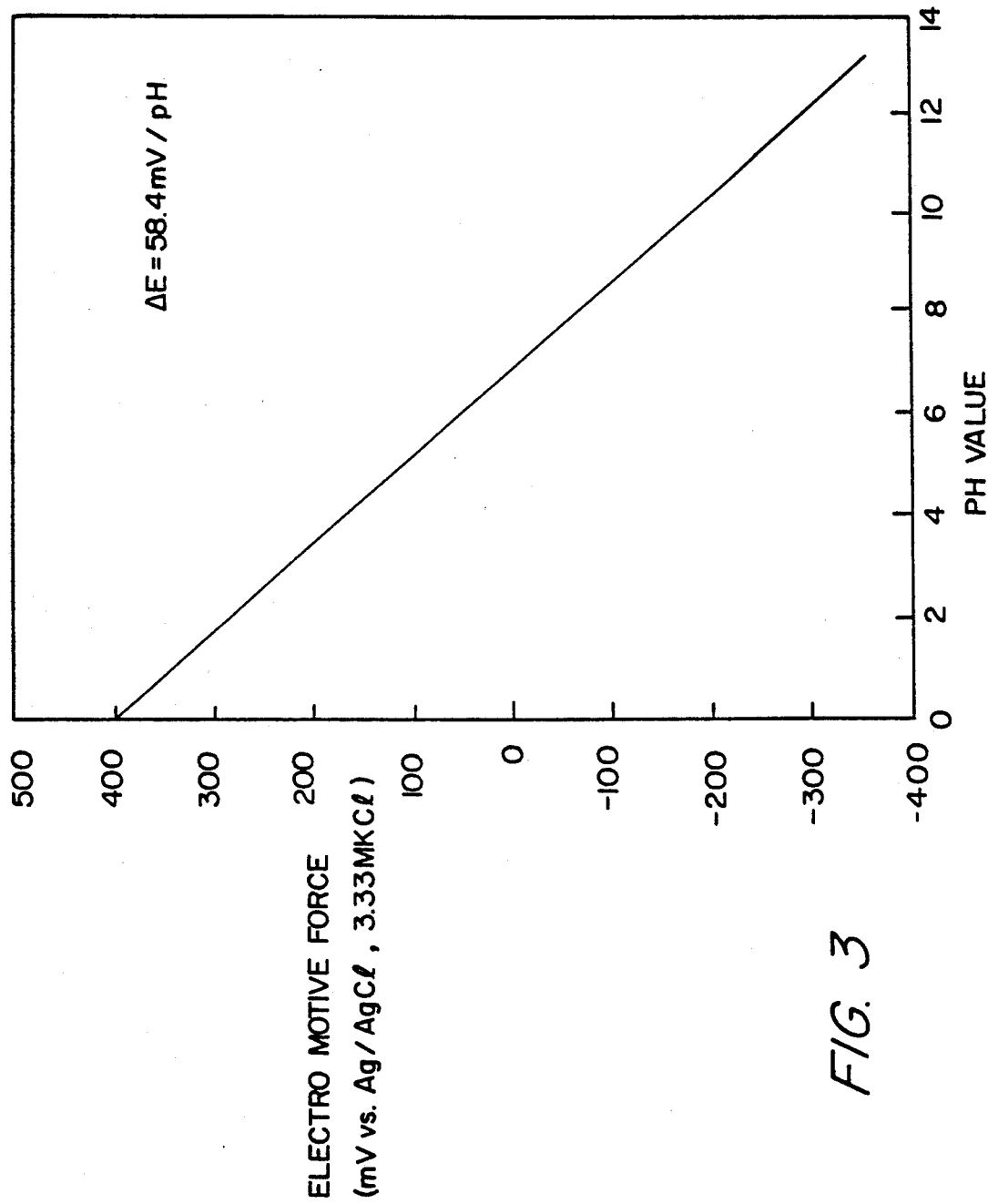
FIG. 3 is a diagram showing the pH responsive characteristics of the pH measuring electrode of the present invention.
Figure 4:
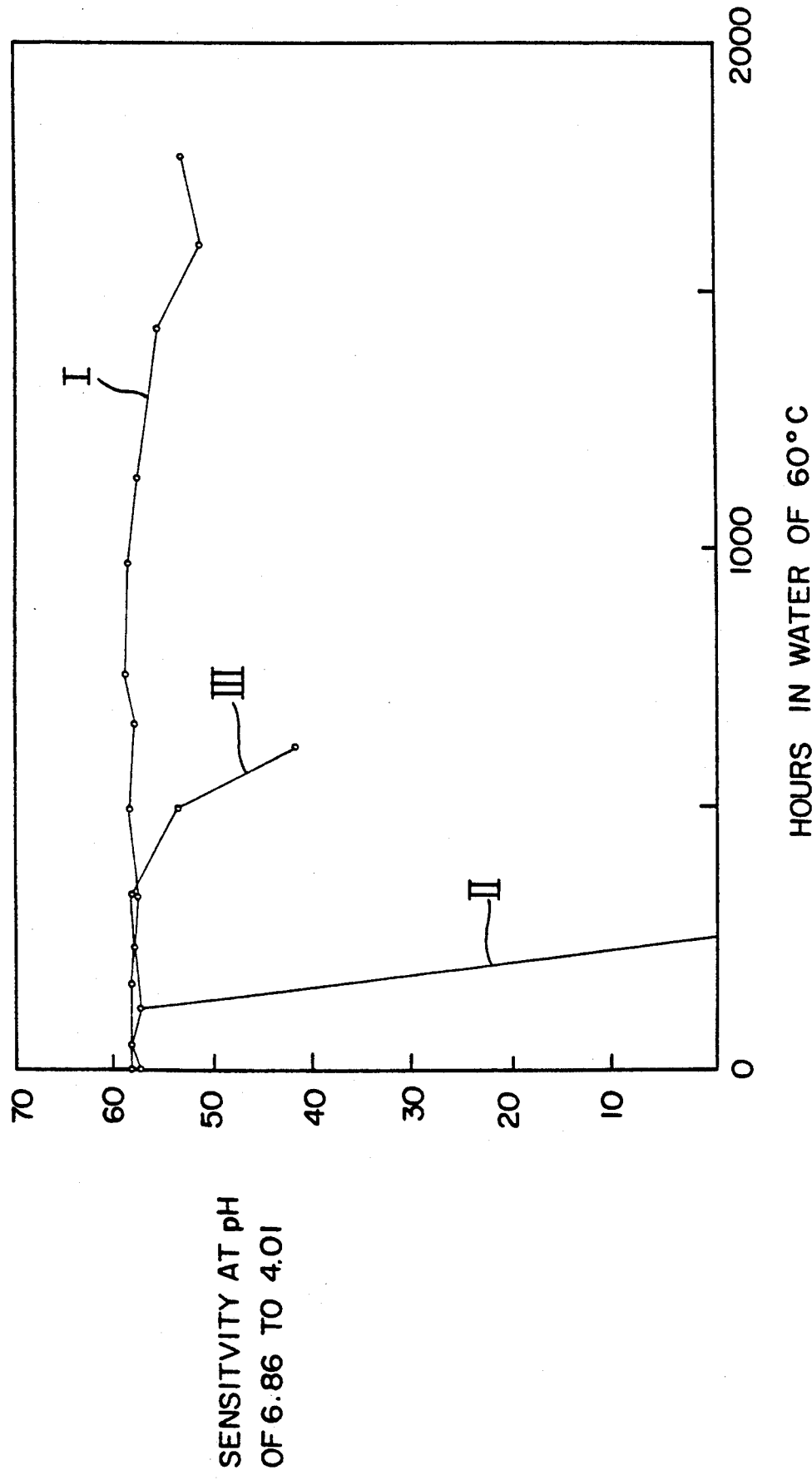
FIG. 4 is a diagram disclosing the effect and sensitivity of the electrode when exposed to high temperature water over a period of time.
Figure 5:
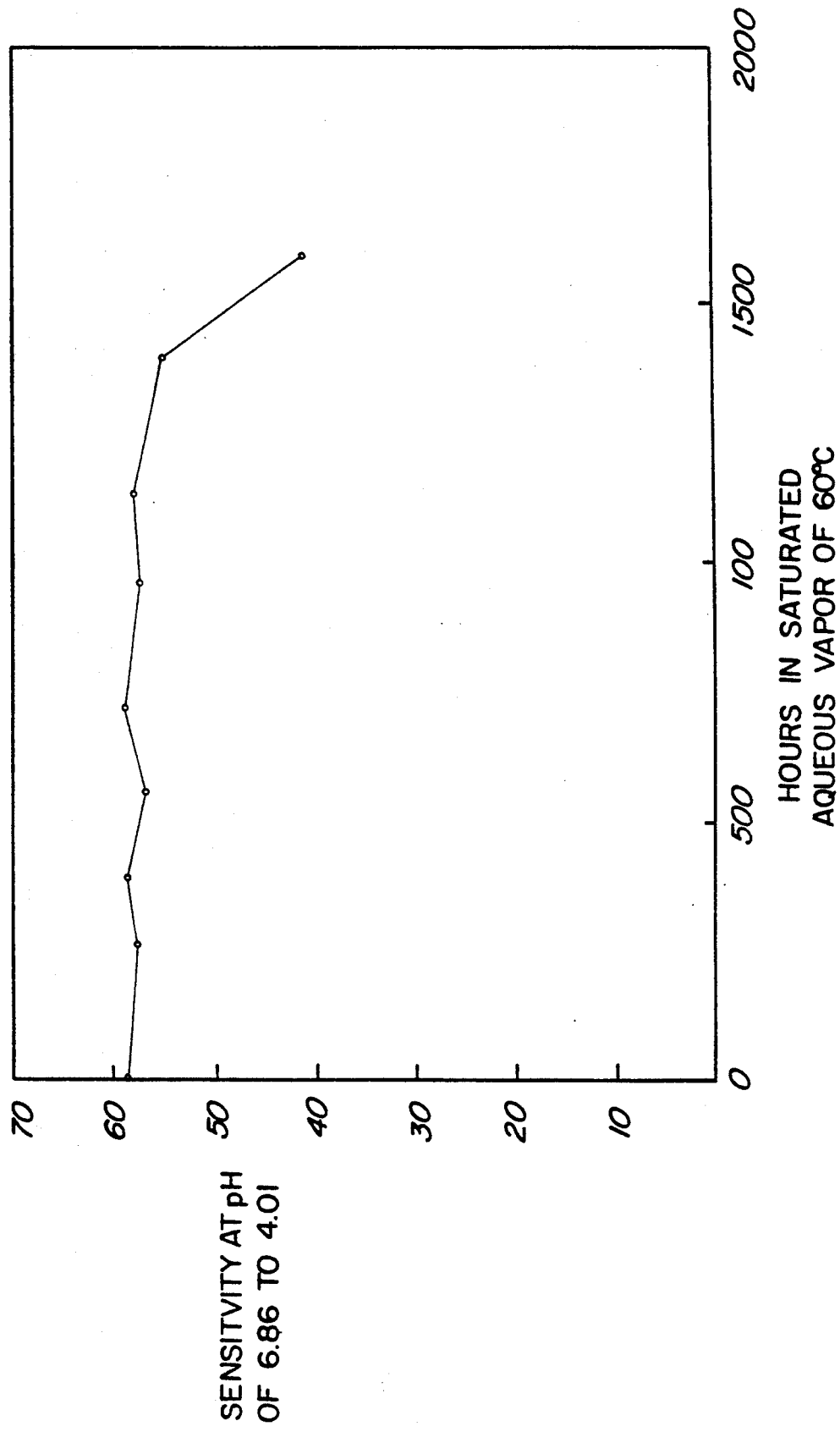
FIG. 5 is a diagram showing the change in sensitivity over a period of time at both high temperature and high humidity.

Reference can be made to FIGS. 3 through 5 to determine the improved characteristics of the ion-responsive electrode of the present invention. Referring to FIG. 3, it is apparent that the pH-responsive characteristics of the pH measuring electrode of the present invention are linear over the entire operative pH range. FIG. 3 is the output from a detector incorporating the electrode for a calibration liquid having a known pH value. The $\Delta E$ value shows the slope which is very close to 59.15 mV/pH which is the theoretical value obtained by the Nernst's equation. To verify the desired durability of the electrode of the present invention, it was subjected to water of a relatively high temperature (ion exchange water of 60° C.). The resulting change of sensitivity in the middle range of the pH meter of 6.86 to 4.0 was investigated, with the result that a curve showing a change of sensitivity, as shown in FIG. 4, was obtained.

Figure 6A:
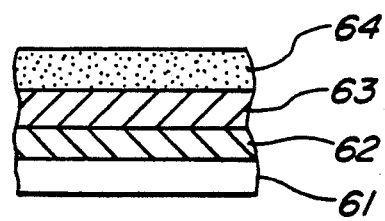
FIGS. 6(A) and 6(B) are longitudinal sectional views showing conventional ion-selective electrode configurations.
Figure 6B:
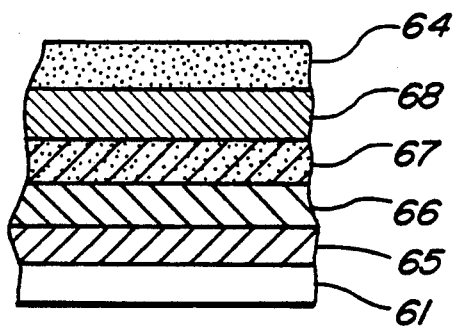

Curve I relates to a pH-measuring electrode manufactured in accordance with the principles of the present invention. Curves II and III relate respectively to pH-measuring electrodes having a construction as shown, respectively, in FIGS. 6(A) and 6(B). As can be readily determined, the durability in water of a relatively high temperature is significantly increased over the prior art pH-measuring electrodes.

Referring to FIG. 5, a measurement again was made of the sensitivity in the pH range of 6.86 to 4.0 over an extended life test in excess of 1400 hours in an environment of a relatively high temperature and humidity, e.g., 60° C. and RH 100%. The curve shown in FIG. 5 discloses the durability of the present invention.

When comparing the respective results of tests in the present invention in FIGS. 4 and 5 over that of the conventional pH-measuring electrodes, it can be seen that an improvement of approximately three times, if not much greater, can be expected. The durability of the measurement capacities of the pH-responsive electrode of the present invention resulted from the improved adhesion of the ion-responsive glass to the substrate through the use of the series of undercoated treated layers 7.

The present invention is not limited by the above-described preferred embodiment, but also can be utilized to produce improvements in Na+-measuring electrodes and K+-measuring electrodes by simply changing the desired composition of the ion-responsive glass 8. Additionally, other forms of adhesives can be utilized, such as CY 50-069 and CY 50-071 made by Toray Silicone KK, and TSE 382 made by Toshiba Silicone KK, as alternative forms of deoximization-type RTV adhesives.

The present invention having the above-described construction has been found to be of particular advantage in providing superior ion-selective electrodes for characteristics of durability and reliability, and further having the capacity to maintain an electrical insulation, even under severe conditions, in relatively economical production procedure.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved ion-selective electrode comprising:
   a substrate of an insulating material;
   a polyethylene terephthalate film layer on the substrate having an aperture;
   an electrically conductive layer positioned on the aperture and extending across the substrate beneath the film layer;
   a series of adhering layers which can be applied above the film layer and around the aperture to form a cavity above the conductive layer, the layer farthest from the substrate being a deoximization silicone room temperature vulcanizing adhesive;
   a gelatinized internal liquid position in the cavity, and
   an ion-responsive glass sheet adhering to the deoximization silicone adhesive and extending over and in contact with the internal liquid.

2. The invention of claim 1 wherein the polyethylene terephthalate film has been pretreated by a corona discharge.

3. The invention of claim 1 wherein the series of adhering layers includes a polyester anchor coating on the polyethylene terephthalate film of approximately 6 to 8 $\mu$m thickness.

4. The invention of claim 3 wherein a polyester hot melt layer of approximately 50 $\mu$m in thickness is applied over the anchor coating.

5. The invention of claim 4 wherein a silicone primer is applied over the hot melt layer.

6. A method of making an improved ion-selective electrode comprising the steps of:
   providing a substrate of an insulating material;
   providing an elastically conductive layer on the substrate;
   laminating a polyethylene terephthalate film layer on the substrate having an aperture;
   depositing a series of adhering layers above the film layer and around the aperture to form a cavity above the conductive layer, the layer farthest from the substrate being a deoximization silicone room temperature vulcanizing adhesive;
   curing the deoximization silicone room temperature vulcanizing adhesive at room temperature for approximately 48 hours;
   applying a gelatinized internal liquid in the cavity, and
   adhering an ion-responsive glass sheet to the deoximization silicone adhesive so that it extends over and in contact with the internal liquid.

7. The invention of claim 6 wherein the polyethylene terephthalate film has been pretreated by a corona discharge.

8. The invention of claim 1 wherein the series of adhering layers includes applying a polyester anchor coating on the polyethylene terephthalate film to approximately 6 to 8 $\mu$m in thickness.

9. The invention of claim 8 including applying a polyester hot melt layer of approximately 50 $\mu$m in thickness over the anchor coating.

10. The invention of claim 9 including applying a silicone primer layer over the hot melt layer.

11. The invention of claim 10 wherein the polyester anchor coating, polyester hot melt layer, and the silicone primer layer are each cured for a few minutes at room temperature before each application of the next layer.

12. An improved ion-selective electrode for use in a relatively high temperature aqueous environment for extended periods of time, comprising:
    a substrate of an insulating material;
    a polyethylene terephthalate film layer on the substrate having an aperture, the film layer characterized as having a surface structure, on each side of the film layer, which has been subject to a corona discharge treatment
    an electrically conductive layer positioned on the aperture and extending across the substrate beneath the film layer;
    a series of adhering layers which can be applied above the film layer and around the aperture to form a cavity above the conductive layer, the layer farthest from the substrate being a deoximization silicone room temperature vulcanizing adhesive that has cured at room temperature for approximately 48 hours;
    a gelantinized internal liquid positioned in the cavity, and
    an ion-responsive glass sheet adhering to the cured deoximization silicone adhesive and extending over and in contact with the internal liquid.

* * * * *